US009026188B2

(12) United States Patent
Taylor et al.

(10) Patent No.: US 9,026,188 B2
(45) Date of Patent: May 5, 2015

(54) MEASUREMENT APPARATUS AND METHOD THEREFOR

(75) Inventors: Robin Taylor, Berkshire (GB); Richard Holley, Berkshire (GB); Austen Hearn, Reading (GB)

(73) Assignee: Lein Applied Diagnostics, Workingham, Berkshire (GB)

( * ) Notice: Subject to any disclaimer, the term of this patent is extended or adjusted under 35 U.S.C. 154(b) by 207 days.

(21) Appl. No.: 12/867,199

(22) PCT Filed: Feb. 9, 2009

(86) PCT No.: PCT/GB2009/050128
§ 371 (c)(1),
(2), (4) Date: Nov. 4, 2010

(87) PCT Pub. No.: WO2009/101433
PCT Pub. Date: Aug. 20, 2009

(65) Prior Publication Data
US 2012/0179380 A1      Jul. 12, 2012

(30) Foreign Application Priority Data

Feb. 11, 2008   (GB) .................................. 0802480.4

(51) Int. Cl.
| A61B 5/00 | (2006.01) |
| A61B 5/1455 | (2006.01) |
| A61B 3/10 | (2006.01) |
| A61B 5/145 | (2006.01) |

(52) U.S. Cl.
CPC ............. *A61B 5/1455* (2013.01); *A61B 3/1005* (2013.01); *A61B 5/14532* (2013.01)

(58) Field of Classification Search
USPC ......................................................... 600/310
See application file for complete search history.

(56) References Cited

U.S. PATENT DOCUMENTS

| 3,963,019 A | 6/1976 | Quandt |
| 4,014,321 A | 3/1977 | March |
| 4,154,114 A | 5/1979 | Katz et al. |
| 4,407,008 A | 9/1983 | Schmidt et al. |
| 4,750,830 A | 6/1988 | Lee |
| 4,806,004 A | 2/1989 | Wayland |
| 4,984,567 A | 1/1991 | Kageyama et al. |
| 5,209,231 A | 5/1993 | Cote et al. |

(Continued)

FOREIGN PATENT DOCUMENTS

| DE | 19632594 A1 | 2/1998 |
| EP | 0485803 A1 | 5/1992 |

(Continued)

OTHER PUBLICATIONS

ASL—Image Analyzer Software, Advanced Scanning, Ltd. Oct. 14, 1999, http://web.archive.org/web/20010722210114/http://advancedscanning.com.*

(Continued)

*Primary Examiner* — Rodeny Fuller
(74) *Attorney, Agent, or Firm* — Bracewell & Giuliani LLP (57) ABSTRACT

A measurement apparatus comprises a probe system (100) operably coupled, when in use, to a processing resource (134). The probe system (100) and the processing resource (134) are arranged, when in use, to measure an apparent thickness change of a volume of the medium (108) to be measured and to determine a physiological parameter using the measurement of the apparent thickness change.

18 Claims, 5 Drawing Sheets

(56) References Cited

U.S. PATENT DOCUMENTS

| | | | |
|---|---|---|---|
| 5,307,203 A * | 4/1994 | Hill | 359/368 |
| 5,433,197 A | 7/1995 | Stark | |
| 5,582,168 A | 12/1996 | Samuels et al. | |
| 5,785,651 A | 7/1998 | Kuhn et al. | |
| 5,839,445 A * | 11/1998 | Kaufman | 128/898 |
| 6,066,847 A | 5/2000 | Rosenthal | |
| 6,152,875 A * | 11/2000 | Hakamata | 600/319 |
| 6,181,957 B1 | 1/2001 | Lambert et al. | |
| 6,187,599 B1 | 2/2001 | Asher et al. | |
| 6,188,477 B1 | 2/2001 | Pu et al. | |
| 6,226,089 B1 * | 5/2001 | Hakamata | 356/432 |
| 6,267,477 B1 | 7/2001 | Karpol et al. | |
| 6,382,794 B1 | 5/2002 | Lai et al. | |
| 6,424,850 B1 | 7/2002 | Lambert et al. | |
| 6,442,410 B1 | 8/2002 | Steffes | |
| 6,574,501 B2 | 6/2003 | Lambert et al. | |
| 6,836,337 B2 | 12/2004 | Cornsweet | |
| 6,853,854 B1 | 2/2005 | Proniewicz et al. | |
| 6,934,035 B2 | 8/2005 | Yang et al. | |
| 7,769,419 B2 * | 8/2010 | Daly | 600/318 |
| 8,078,245 B2 * | 12/2011 | Daly et al. | 600/319 |
| 2002/0171804 A1 | 11/2002 | Rathjen | |
| 2003/0225321 A1 | 12/2003 | Cote et al. | |
| 2003/0233036 A1 | 12/2003 | Ansari et al. | |
| 2004/0080759 A1 * | 4/2004 | Shaver | 356/609 |
| 2004/0087843 A1 | 5/2004 | Rice et al. | |
| 2004/0138539 A1 | 7/2004 | Jay et al. | |
| 2004/0152963 A1 | 8/2004 | March | |
| 2004/0257585 A1 | 12/2004 | Cornsweet | |
| 2007/0078308 A1 * | 4/2007 | Daly | 600/310 |
| 2007/0123761 A1 * | 5/2007 | Daly et al. | 600/316 |
| 2007/0255141 A1 | 11/2007 | Esenaliev | |
| 2011/0043661 A1 * | 2/2011 | Podoleanu | 348/239 |

FOREIGN PATENT DOCUMENTS

| | | |
|---|---|---|
| EP | 0589191 A1 | 3/1994 |
| EP | 0722692 A1 | 7/1996 |
| EP | 0792619 A1 | 9/1997 |
| EP | 0807812 A1 | 11/1997 |
| EP | 0810457 A1 | 12/1997 |
| GB | 1521113 | 8/1978 |
| GB | 2144537 A | 3/1985 |
| GB | 2407378 A | 4/2005 |
| GB | 2409033 A | 6/2005 |
| JP | 3055510 A | 3/1991 |
| JP | 2000139841 A | 11/1998 |
| WO | WO92/01417 | 2/1992 |
| WO | WO93/07801 | 4/1993 |
| WO | WO97/13448 | 4/1997 |
| WO | WO97/30627 | 8/1997 |
| WO | WO99/44496 | 9/1999 |
| WO | WO00/60350 | 10/2000 |
| WO | WO02/087429 A1 | 11/2002 |
| WO | WO03/012486 A2 | 2/2003 |
| WO | WO03/087775 A2 | 10/2003 |
| WO | WO2004/030530 A1 | 4/2004 |
| WO | WO2004/034894 A1 | 4/2004 |
| WO | WO2004/064628 A1 | 8/2004 |
| WO | 2004089198 A1 | 10/2004 |
| WO | WO2005/120334 A1 | 12/2005 |

OTHER PUBLICATIONS

Pierro, et al., Correlation of corneal thickness with blood glucose control in diabetes mellitus, Acta Ophthalmologica, vol. 71, Issue 2, pp. 169-172, Apr. 1993 (abstract).*

Busted, et al., Clinical observations on the corneal thickness and the corneal endothelium in diabetes mellitus, British J. of Ophthalmology, 1981, 65, 687-690.*

McNamara, et al., Corneal Function during Normal and High Serum Glucose Levels in Diabetes, Investigative Ophthalmology & Visual Science, Jan. 1998, vol. 39, No. 1.*

Jie Li et al., "On-Line 3-Dimensional Confocal Imaging in Vivo," Investigative Ophthalmology & Visual Science, Sep. 2000, vol. 41, No. 10, pp. 2945-2953.

Barry R. Masters et al., "Three-Dimensional Confocal Microscopy of the Living Human Eye," Universitats-Augenklinik, Inselspital, University of Bern, 3010 Bern, Switzerland, Annual Rev. Biomed. Eng., 2002, vol. 4, pp. 69-91.

Jay W. McLaren, PhD., et al., Corneal Thickness Measurement by Confocal Microscopy, Ultrasound, and Scanning Slit Methods, American Journal of Opthalmology, Jun. 2004, vol. 137, No. 6.

Hong Fang Li, et al., Epithelial and Corneal Thickness Measurements by In Vivo Confocal Microscopy Through Focusing (CMTF), Current Eye Research, Department of Ophthalmology, University of Texas Southwestern Medical Center, Dallas, TX, et al., Oxford University Press, 1996, pp. 214-221.

Daniel H. W. Su, Tien Y. Wong, Wan-Ling Wong, Seung-Mei Saw, Donald T.H. Tan, Sunny Y. Shen, Seng-Chee Loon, Paul J. Foster, and Tin Aung; "Diabetes, Hyperglycemia, and Central Corneal Thickness"; The Singapore Malay Eye Study; Aug. 10, 2007; pp. 964-968. e1; Manuscript No. 2007-472; American Academy of Ophthalmology, Published by Elsevier Inc.; USA.

* cited by examiner

MEASUREMENT APPARATUS AND METHOD THEREFOR

The present invention relates to a measurement apparatus of the type that, for example, is used to provide measurements in relation to properties relating to a volume of a medium in order to provide a measure of a physiological parameter, such as an ophthalmic measurement to determine a blood-glucose concentration level. The present invention also relates to a method of measuring a property of a volume of a medium of the type that, for example, is used to provide non-invasive measurement of a physiological parameter, such as ophthalmic measurement to determine a blood-glucose concentration level.

Diabetes is a major and rapidly growing problem with over 245 million people suffering from the disorder worldwide. In addition, studies have shown that the incidence of juvenile-onset, insulin-dependent diabetes doubled over a 15 years period leading up to 2003. There was also a five fold increase in the number of children under the age of 5 suffering from diabetes in the 20 year period leading up to 2003.

The symptoms associated with diabetes can be severe. If the blood glucose level is not suitably controlled by the patient, the physical damage which may be caused includes blindness, heart disease and gangrene. As such, the mortality rate for people with diabetes is significantly higher than the rate for the average person.

A person's blood glucose concentration varies over a relatively short timescale, due to a number of factors, such as the length of time since the patient's last meal, the type of food ingested, the amount of exercise taken, and whether or not the patient is otherwise ill. As a result, people with diabetes usually need to test their glucose concentration levels many times a day, in order to monitor and control their condition. The actual testing regime varies between patients and is individually prescribed by the doctor or diabetes educator of the patient.

The primary method used for testing blood glucose concentration involves the taking of a blood sample, which is then analysed. In this test, a patient's finger or arm is pricked with a small needle and the resulting drop of blood is placed on a test strip, for analysis in a hand-held meter. If the glucose concentration reading is above an acceptable level, insulin must be injected to bring the glucose concentration back down to within an acceptable range.

Due to the frequency of testing required to monitor the blood glucose concentration, the patient is normally expected to perform the tests throughout the day, drawing and analysing the blood sample himself. There are a number of problems experienced by patients with the above procedure. Firstly, the technique is invasive and therefore carries the risk of infection. Secondly, continual pricking of the fingers causes hard skin. Thirdly, the process is clearly not pain-free. Finally, there is a large, ongoing consumables cost associated with this method. As a result of these and other problems, certain sectors of the diabetic population do not test themselves as often as required. This is particularly the case for the elderly, who tend to lack the fine motor skills required; teenagers, who tend to find the whole procedure socially embarrassing; and children, who tend not to accept the discomfort associated with the process.

A number of non-invasive blood glucose concentration measuring techniques have been proposed to overcome these problems. In general these have been designed to work by making a measurement through the skin but the variability in the skin's characteristics have led to inaccurate results.

More recently the eye has been proposed as a better measurement location. Possible techniques for measuring glucose in the eye include spectroscopy on the conjunctiva (e.g. U.S. Pat. No. 6,975,892), psychophysical measurements on the fundus (e.g. U.S. Pat. No. 6,895,264), a contact lens or other implantable device that absorbs glucose (e.g. U.S. Pat. No. 6,980,842 or US 2006/0166350) or a measurement of the ocular refractive correction (e.g. U.S. Pat. No. 6,442,410).

One particular approach which has been suggested involves measuring the glucose concentration of the aqueous humour in the anterior chamber of the eye, since, while varying between individuals, there is a close correlation between this concentration and the blood glucose concentration. Measurement of the glucose concentration of the aqueous humour may be achieved by various means; for example, by polarimetry (e.g., U.S. Pat. No. 5,896,198); by Raman techniques (e.g., WO A 00/02479); by fluorescence photometry (e.g., WO 2005/120334); by spectrometry (e.g., U.S. Pat. No. 5,969,815); by fluorescence spectroscopy (e.g., WO 02/087429) or by reflectometry (e.g., U.S. Pat. No. 6,236,089).

A desirable alternative approach to measuring the glucose concentration in the aqueous humour involves measuring the refractive index of the aqueous humour, since there is a strong correlation between the refractive index and the glucose concentration. In this respect, U.S. Pat. No. 3,963,019, U.S. Pat. No. 6,152,875, WO 03/025562, WO 05/044099, WO 05/058152, GB-B-2 407 378 and GB-A-2 409 033 describe various techniques associated with measurement of the refractive index of the aqueous humour.

Of course, the above-described techniques suffer from limitations in respect of reliability when attempting to measure a physiological parameter, for example the blood-glucose concentration level. In particular, polarimetry suffers from interference due to birefringence of the cornea. Interference is also problematic in relation to fluorescence-photometry and spectroscopy, the interference being generated in a measurement signature by other molecules in the eye. Also, when employing techniques reliant upon measurement of a refractive index, changes to boundaries with the aqueous humour cause measurement results to alter from actual values.

According to a first aspect of the present invention, there is provided a measurement apparatus comprising: a probe system operably coupled, when in use, to a processing resource, the probe system and the processing resource being arranged, when in use, to measure a thickness of a volume of a medium to be measured and determine an apparent thickness change thereof, and to determine a physiological parameter using the measurement of the apparent thickness change.

It should be appreciated that reference herein to a "medium" is intended to be construed, where context permits, as a reference to "tissue" or "fluid". References herein to an apparent thickness change is intended to refer to a thickness that appears to exist when measurement occurs and should also be interpreted to embrace an actual thickness change. A number of reasons for a thickness change to be apparent may exist, for example due to a refractive index change and/or an actual physical thickness change.

The probe system may be an optical system. The apparent thickness change of the volume of the medium may be in respect of a target portion of the medium. The medium may be tissue or fluid. The medium may be corneal tissue. A cornea may comprise the corneal tissue.

A correlation or regression may exist between the apparent thickness change of the volume of the medium and the physiological parameter.

The apparent thickness may be between a first surface and a second surface of the medium.

The probe system may comprise: a source arranged to emit, when in use, a probe beam, the probe system being arranged to direct the probe beam to a first location and a second location in respect of a region to be measured.

The processing resource may be coupled to a detector; the detector may be capable of translating an optical signal into an electrical signal.

The probe system may further comprise: a detector arranged to receive, when in use, a first reflected beam from the first location and a second reflected beam from the second location.

The processing resource may be arranged to measure, when in use, an apparent change in thickness between the first and second locations using the first and second reflected beams in order to determine the structural change of the volume of the medium.

The probe system may be arranged to generate a trace in response to electromagnetic radiation received thereby. The processing resource may be arranged to identify a first localised maximum in the trace and a second localised maximum in the trace.

The first localised maximum may be associated with the first reflected beam and the second localised maximum may be associated with the second reflected beam.

The processing resource may be arranged to calculate a distance between the first localised maximum and the second localised maximum. The distance between the first and second localised maxima may correspond to the apparent thickness of the volume of the medium.

The processing resource may be arranged to locate the first localised maximum by fitting a first curve thereto. The processing resource may be arranged to locate the second localised maximum by fitting a second curve thereto. The curve fitting may be fitting of a Gaussian profile or a Sinc profile.

The processing resource may be arranged to calculate the apparent thickness change of the volume of the medium over time.

The probe system may be arranged to determine a first apparent thickness in respect of the tissue at a first point in time and a second apparent thickness in respect of the tissue at a second point in time. The processing resource may be arranged to calculate an integral of the apparent thickness of the volume of the medium between the first and second points in time.

The apparatus may further comprise a data store for recording calibration data, the processing resource being arranged to use the calibration data to compensate for patient-specific cornea thickness when determining the physiological parameter.

The probe system and the processing resource may be arranged to use multiple sites on the medium to determine the changes in apparent thickness of the volume. The multiple sites may be employed to generate the first apparent thickness at the first point in time and the same multiple sites may be respectively employed to generate the second apparent thickness at the second point in time.

The processing resource may be arranged to provide an expected apparent thickness of the volume of the medium at a time of measurement. The processing resource may be arranged to employ a function to calculate the change in apparent thickness of the volume of the medium associated with the physiological parameter using the expected apparent thickness and a measurement of the thickness of the volume of the medium. The function may be a difference calculation between the expected apparent thickness and the measured apparent thickness.

The expected apparent thickness may be obtained from a change in apparent thickness of the volume of the medium over time.

The expected apparent thickness may be obtained from a data set derived from empirical data of change in apparent thickness of the volume of the medium over time.

The expected apparent thickness may be obtained from a model of apparent thickness over time. The model may use a measured value as an input for calculating the expected apparent thickness.

According to a second aspect of the present invention, there is provided an optical measurement apparatus comprising the measurement apparatus as set forth above in relation to the first aspect of the invention.

According to a third aspect of the present invention, there is provided a glucometer comprising the measurement apparatus as set forth above in relation to the first aspect of the invention.

According to a fourth aspect of the present invention, there is provided a method of measuring a property of a medium, comprising: probing a volume of a medium to be measured in order to receive a feedback signal; measuring an apparent thickness of the volume of the medium using the feedback signal; determining an apparent thickness change of the volume of the medium; and determining a physiological parameter using the measurement of the apparent thickness change.

According to a fifth aspect of the present invention, there is provided a computer program element comprising computer program code means to make a computer execute the method as set forth above in relation to the fourth aspect of the invention.

The computer program element may be embodied on a computer readable medium.

According to a sixth aspect of the invention, there is provided a method for determining a blood-glucose concentration level, comprising: detecting an apparent change in the thickness of corneal tissue and translating the change in the apparent thickness of the corneal tissue into the blood-glucose concentration level.

Translation of the apparent change in the thickness of the corneal tissue into the blood-glucose concentration level may comprise accessing a translation entity, for example a look-up table or a mathematical function.

It is thus possible to provide a measurement apparatus and method that enables a physiological parameter to be measured, for example levels of a chemical, such as a pharmaceutical composition, including both naturally occurring and intentionally introduced chemicals, such as a blood-glucose concentration level in a bloodstream. The accuracy and reliability of measurements made using the measurement apparatus is improved in relation to known apparatus and techniques. Furthermore, where the measurement apparatus is confocal in nature, measurement is insensitive to changes occurring outside a region to be measured.

At least one embodiment of the invention will now be described, by way of example only, with reference to the accompanying drawings, in which.

Throughout the following description identical reference numerals will be used to identify like parts or steps.

Figure 1:
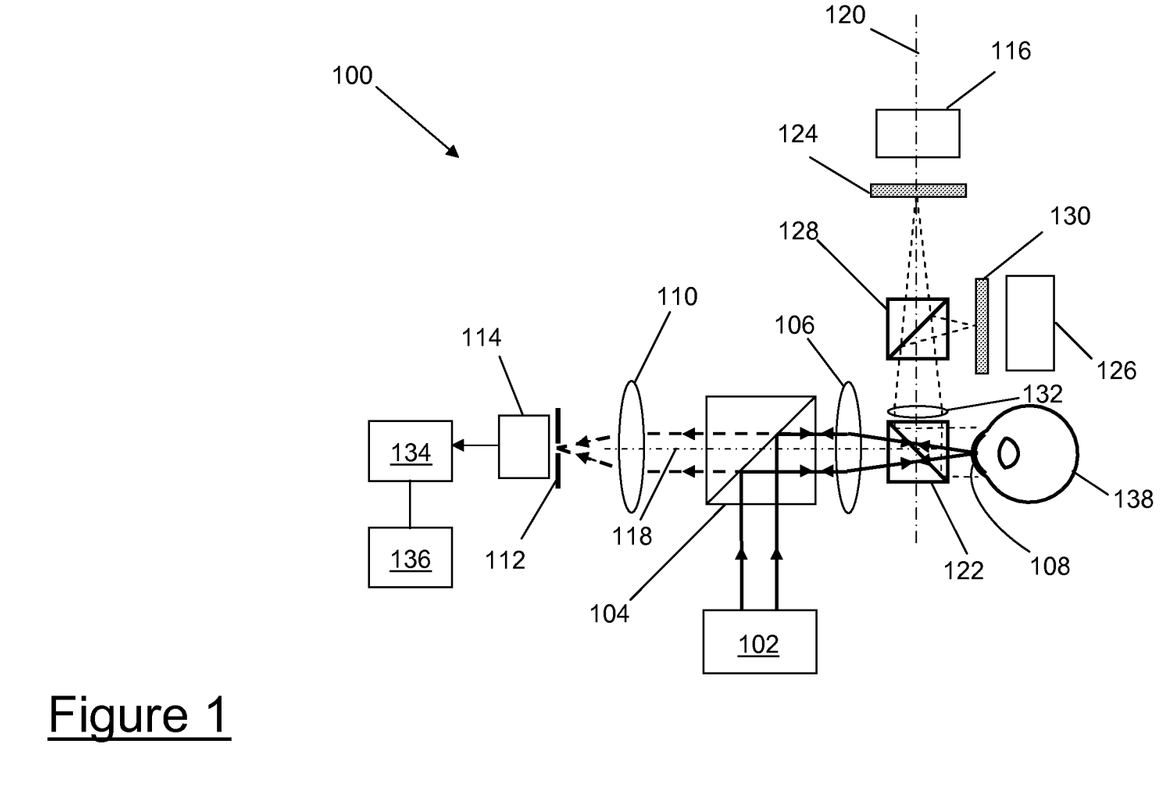
FIG. 1 is a schematic diagram of a measurement apparatus constituting an embodiment of the invention.

Referring to FIG. 1, an optical measurement apparatus, for example a glucometer, comprises an optical system 100 including a first source 102 of electromagnetic radiation, for example visible light, though light invisible to the eye, for example infra-red light, can be used so as to reduce discomfort when a measurement is to be made in relation to an eye. An output window (not shown) of the first source 102 is oriented towards a first beamsplitter 104 that is placed in an optical path of the first source 102. The first beamsplitter 104 serves to fold the optical path of the first source 102 towards a scanning lens 106. In this example, the scanning lens 106 is shown as a single lens, though the skilled person will appreciate a lens system can serve as the scanning lens 106 or any other suitable optical arrangement, scanning or non-scanning in nature for making measurements. The scanning lens 106 is capable of linearly translating so as to move optically closer to or further from a region to be measured 108 in accordance with UK patent publication no. GB-B-2 407 378. The first beamsplitter 104 is a half-silvered mirror, though the skilled person will appreciate that any suitable alternative optical element or arrangement can be employed to function as the first beamsplitter 104, for example a polarising beamsplitter and ¼ wave plate disposed between the polarising beamsplitter and the scanning lens 106.

A first focussing lens 110 is disposed opposite the first beamsplitter 104 so that the first beamsplitter 104 is located between the scanning lens 106 and the first focussing lens 110. As the optical measurement apparatus is, in this example, a confocal system, an aperture 112 constituting a pinhole is disposed opposite the first focussing lens 110, a detector 114 being disposed adjacent the aperture 112. The detector 114, in this example, comprises a photodiode (not shown in FIG. 1).

In order to align the optical system 100 with the location to be measured, the optical system 100 comprises an alignment arrangement. Any suitable alignment arrangement can be employed and a number of such alignment arrangements are described in co-pending UK patent application no. 0714736.6, the content of which is incorporated herein by reference. One example of the alignment arrangement will now be described for the sake of completeness.

The alignment arrangement comprises a second source 116 of electromagnetic radiation placed away from an optical receiving axis 118 of the optical system 100. In this example, the second source 116 is aligned with a perpendicular alignment axis 120 that meets the optical axis 118 at a second beamsplitter 122. However, other, non-perpendicular, alignment axes can be employed instead of the perpendicular alignment axis 120, for example a Brewster alignment axis. A first graticule 124 is disposed in front of the second source 116. A third source 126 of electromagnetic radiation is disposed perpendicularly with respect to the perpendicular alignment axis 120 and directed at a third beamsplitter 128 disposed in the perpendicular alignment axis 120 between the second beamsplitter 122 and the first graticule 124. A second graticule 130 is disposed between the third source 126 and the third beamsplitter 128. A second focussing lens 132 is also placed in the perpendicular alignment axis 120 adjacent the second beamsplitter 122 so as to be located between the second and third beamsplitters 122, 128. The skilled person will again appreciate that the second focussing lens 132 can be any suitable lensing arrangement to generate a nominally parallel beam at the region to be measured 108.

The first and second graticules 124, 130 are configured so as to define respective shapes, for example cross-hairs or circles of the same or differing sizes.

The skilled person will appreciate that the first and second graticules 124, 130 can be a first display device and a second display device, the first display device being capable of generating a first alignment marker image (not shown) and the second display device being capable of generating a second alignment marker image (not shown) to be viewed by an eye. In particular, the eye has a first axis, for example an optical axis, to be aligned with the optical receiving axis 118 of the optical system 100. In this example, the first display device is a first Liquid Crystal Display (LCD) device and the second display device is a second LCD device. However, the skilled person will appreciate that other imaging devices can be employed, for example one or more Spatial Light Modulators (SLMs). In the present example, the second and third sources 116, 126 and the first and second graticules 124, 130 constitute a source of the first and second alignment marker images.

A processing resource, for example a microprocessor 134, is coupled to the detector 114. The processor 134 is also coupled to a storage device 136, for example a digital memory device, such as a Flash Memory. The storage device 136 is used to record, at least temporarily, data concerning measurement of the blood-glucose concentration of the patient, for example traces, distances and a calibration factor. In this example, the processor 134 and the storage device 136 are part of a general-purpose computing device, for example a Personal Computer (PC). However, the skilled person should appreciate that other implementations, for example a hand-held implementation, can comprise a Digital Signal Processor (DSP) coupled to the digital memory 136 in place of the general-purpose computing device.

In operation (FIG. 2), a user, for example a patient, brings the eye to the measurement apparatus and a measurement procedure is initiated by pressing a "measure" button (not shown) on the apparatus, which causes the processing resource 134 to initiate an alignment procedure (Step 200) in order to align the optical axis 118 of the optical system 100 to an axis of the eye. In this example, alignment is to the optical axis of the eye, though a visual axis of the eye or any other suitable axis can be employed in this or other implementations. For the sake of completeness, one example of the alignment procedure is described hereinbelow. However, further examples are set out in the co-pending UK patent application no. 0714736.6 mentioned above.

Figure 2:
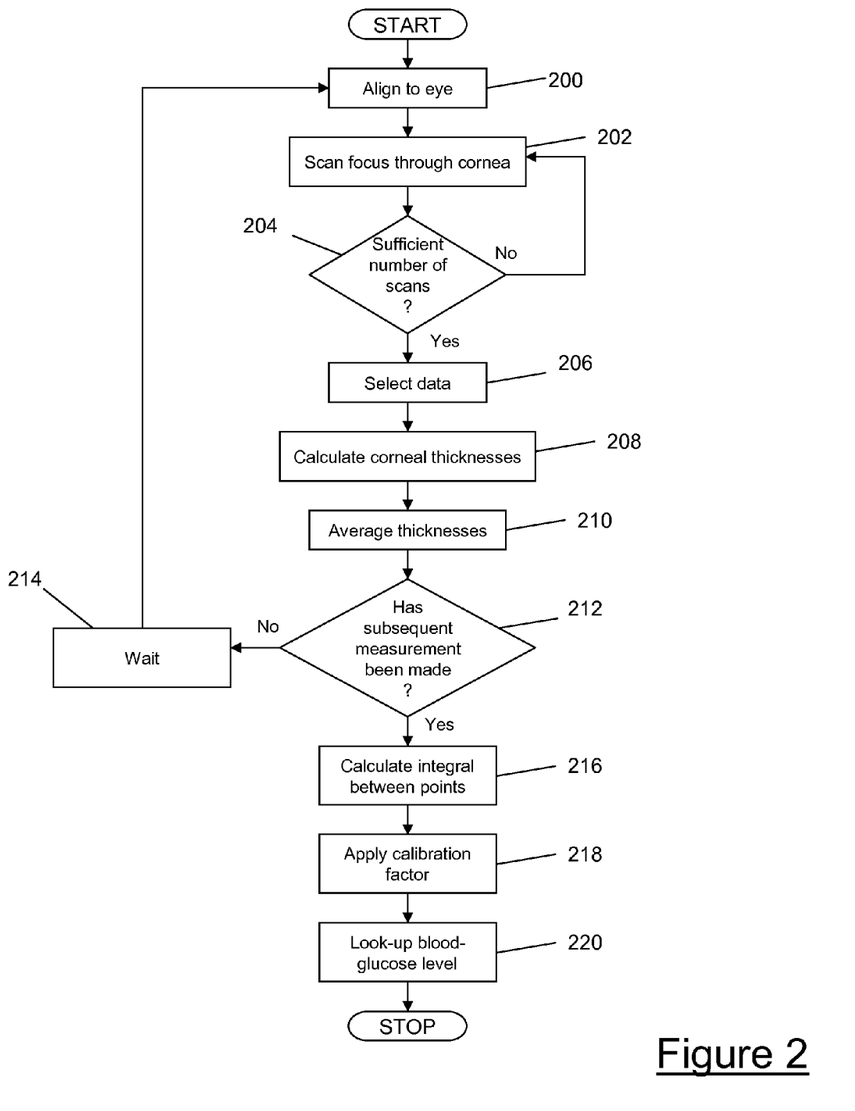
FIG. 2 is a flow diagram of a method of measuring a physiological parameter using the apparatus of FIG. 1.

The second and third sources 116, 126 emit light that passes through the first and second graticules 124, 130 or display devices, respectively to provide a first image beam and a second image beam which are incident upon the third beamsplitter 128 and combined before passing through the second focussing lens 132. Thereafter, the combined beams are directed by the second beamsplitter 122 to the region to be measured 108 in, in this example, the eye 138. The first alignment marker image is generated so as to appear at a first focal distance from the eye 138 and the second marker image is generated so as to appear at a second focal distance from the eye 138, the first and second alignment marker images appearing superimposed or coaxial when viewed along the optical receiving axis 118 of the optical system 100.

A first axis (not shown) of the eye 138 is typically initially not aligned with the optical receiving axis 118 of the optical system 100. Consequently, a field of view of the eye 138 sees the first and second marker images spatially separated from each other as a result of parallax.

If the eye 138 is then moved, for example by moving the head and/or the eye 138 in its socket, in an attempt to cause the first and second alignment images to become superimposed, the first axis of the eye 138 becomes aligned with the optical receiving axis 118 of the optical system 100. In this respect, one of the first and second alignment marker images can be stationary so as to serve, for example, as a reference and another of the first and second alignment marker images can appear to move in response to movement of the eye 138 relative to the optical receiving axis 118.

Once aligned, a measurement can be made in respect of the region to be measured 108, now aligned with the optical receiving axis 118 of the optical system 100. In this respect, the techniques set forth in UK patent publication no. GB-B-2 407 378 and/or GB-A-2 409 033 are/is employed to scan (Step 202) a focus of the optical system 100 through the eye 138. In this respect, the focus is scanned through the region to be measured 108, the scans starting outside one boundary of the region to be measured 108 and ending outside another boundary of the region to be measured, i.e. the start and end points of the scan are either side of the region to be measured 108. Consequently, in this example, the scan commences slightly outside the eye, for example 2 mm or less, such as 1 mm, and terminates slightly outside the maximum expected interface between the aqueous humour and the cornea, for example 2 mm or less, such as 1 mm outside.

A first collimated probe beam 140 is therefore generated by the first source 102 and folded by the first beamsplitter 104. The folded first beam 140 is thus directed towards the eye 138 along the optical axis 118, propagating through the second beamsplitter 122. Translation of the scanning lens 106 enables the focus of the folded first probe beam 140 to be scanned through the eye 138 in the manner described above.

Figure 3:
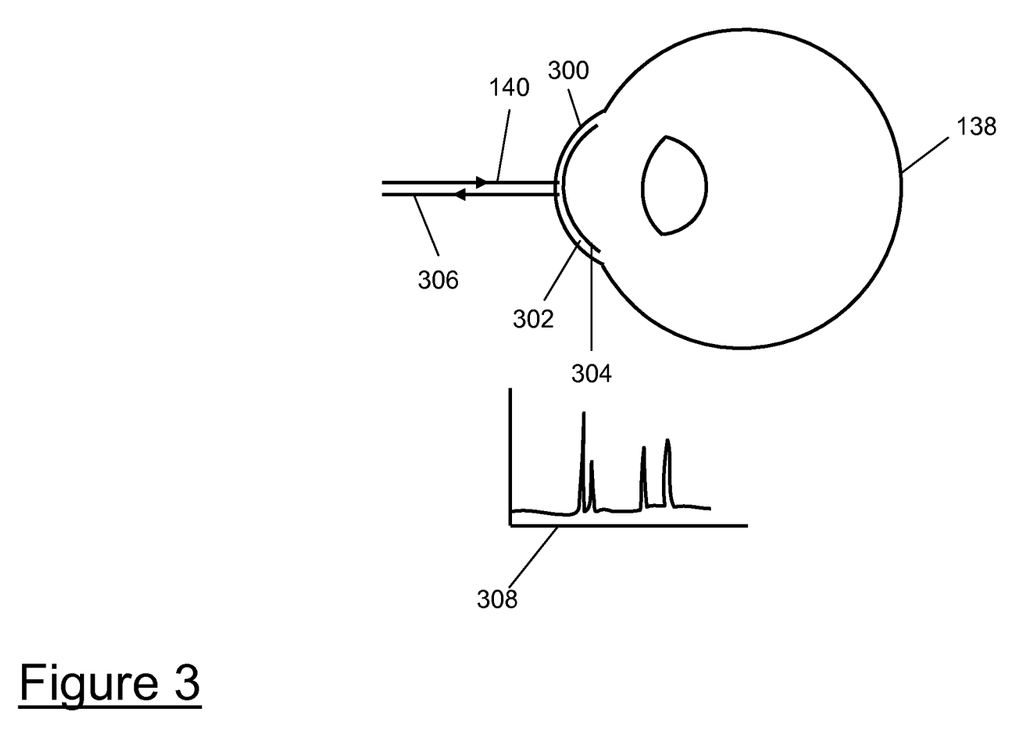
FIG. 3 is a schematic diagram of incident and reflected beams with respect to an eye using the apparatus of FIG. 1.

Referring to FIG. 3, as the focus of the optical system 100 is scanned through the eye 138, and in particular the region to be measured 108, the first probe beam is reflected, firstly, by an anterior surface 300 of the cornea 302 of the eye 138, and subsequently by a posterior surface 304 of the cornea 302. A time-varying first reflected beam 306 therefore results that passes back through the second beamsplitter 122 and the scanning lens 106. The scanning lens 106 collimates the first reflected beam 306, which passes through the first beamsplitter 104 and is focussed onto the detector 114 via the aperture 112 by the focussing lens 110. The detector 114 translates the first reflected beam 306, constituting an optical signal, from the optical domain into the electrical domain. Consequently, the processor 134 receives an electrical signal in the form of a first time-varying trace 308 comprising localised maxima, for example, peaks created by reflections at the anterior and posterior surfaces 300, 304 of the cornea 302.

The processor 134 then determines (Step 204) whether a sufficient number of scans have been executed for signal processing purposes. In this example, 30 scans are implemented and the resulting first set of traces stored in the storage device 136. However, the skilled person will appreciate that a greater or fewer number of traces can be executed depending upon the signal processing requirements for the use to which the measurement apparatus is to be put.

Figure 4:
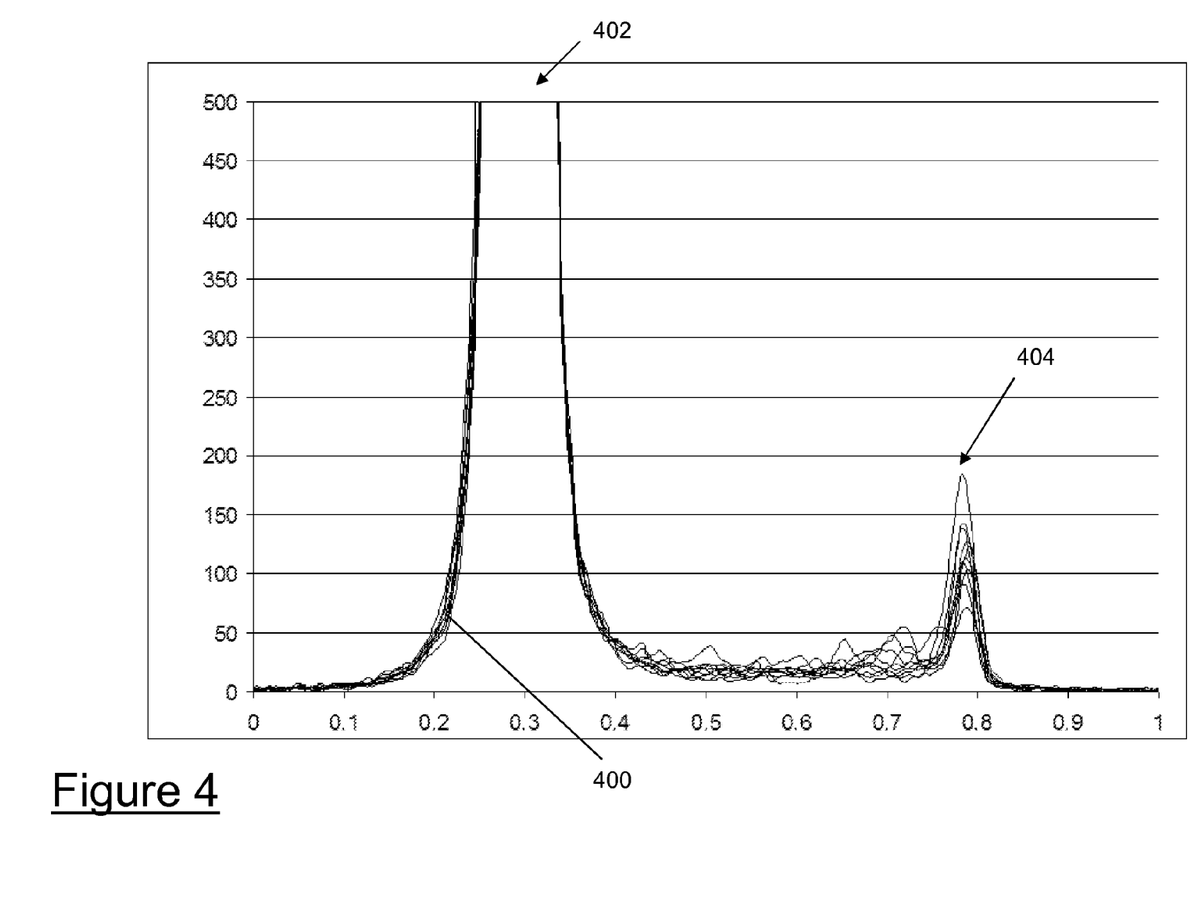
FIG. 4 is a schematic diagram of multiple traces obtained using the apparatus of FIG. 1.

Once multiple first scans have been executed, the stored first scans are analysed by the processor 134 and first scans that have signal levels within predetermined thresholds are selected (Step 206), the remaining scans being deemed aberrant or inadequate in other ways and rejected. Thereafter, the processor 134 analyses each of the remaining first traces 400 (FIG. 4) and identifies a first localised maximum 402 and a second localised maximum 404 indicative of the reflection of the first probe beam 140 by the anterior surface 300 of the cornea 302 and the posterior surface 304 of the cornea 302, respectively. As part of the analysis, the processor 134 calculates the apparent distance (Step 208) between the first and second localised maxima 402, 404 of each of the remaining first traces 400, the distance corresponding to the apparent thickness of the cornea 302. In order to improve consistency of measurements when calculating inter-peak distances, one or more portions of the trace associated with the first localised maximum 402 and/or the second localised maximum 404 can be modelled, for example by fitting a curve, such as a Gaussian profile or a Sinc profile, in order to better locate the first localised maximum 402 and/or the second localised maximum 404.

Thereafter, the processor 314 performs a mathematical process, for example the calculation of an average (Step 210) of the distances calculated above, to yield an accurate apparent first thickness.

The processor 134 then determines (Step 212) whether a second measurement has already been made. In this example, the second measurement has not yet been made and so the processor 134 waits a predetermined amount of time (Step 214) as dictated by a user based upon clinical advice before re-executing the alignment and scanning process. The amount of time waited between conducting sets of scans can vary in a range from a few minutes, for example 15 minutes, to one or more hours. However, once the waiting period has expired, then the alignment and scanning process is re-executed to generate a second probe beam that results in a second reflected beam that is translated into a second electrical time-varying trace having respective first and second localised maxima (Steps 200, 202). As described in relation to the first execution of the measurement process, multiple second scans are generated and traces corresponding to undesirable scans selectively eliminated to result in a second set of traces that are used to calculate a second set of thicknesses of the cornea 302 (Steps 204 to 208). The second set of apparent distances are also then averaged (Step 210) to yield an averaged apparent second thickness. Thereafter, the two time-separated averaged thicknesses calculated are used by the processor 134 to calculate an integral (Step 216) of the apparent thickness of the cornea 302 over the time separation between making the two measurements mentioned above. One exemplary measurement programme comprises a patient making an initial measurement shortly after waking up in the morning and then making measurements at regular internals thereafter, for example every hour. The patient can also make supplementary measurements before and/or after meals. The measurements of apparent thickness of the cornea can be referenced to a time. Consequently, an initial or early measurement in a waking day of a patient can be used as a baseline measurement for subsequent comparative purposes and thereby acts as a reference.

The processor 134 then retrieves the calibration factor from the storage device 136 and applies the calibration factor (Step 218) to the calculated integral. The calibration factor is a predetermined corneal thickness associated with the patient and used to shift measured data so as to calibrate the measured data with the blood-glucose concentration measurement. The calibration factor has a period of validity due to potential changes that can occur in the eye, for example due to paediatric development. Consequently, the calibration factor should be updated at time intervals, for example every 3 months, 6 months or 1 year, or any other suitable interval as clinical prudence may dictate. A corrected integral value therefore results that corresponds to a blood-glucose concentration of the patient using the measurement apparatus. In order to translate the corrected integral value to a blood glucose concentration value, the processor 134 accesses the data store 136 and uses, in this example, a look-up table of corrected integral values and corresponding blood-glucose concentrations, and determines (Step 220) a blood-glucose concentration level corresponding to the corrected integral value calculated above. In this respect, it has been discovered that apparent corneal thickness of a patent varies over time with blood-glucose concentration level of the patient. Of course, instead of using the look-up table, the blood-glucose concentration value could be obtained by way of a function that calculates the blood-glucose concentration according to a predefined algorithm using the corrected averaged value as an input due to the consistency with which blood-glucose concentration level and corneal thickness have been observed to vary.

Figure 5:
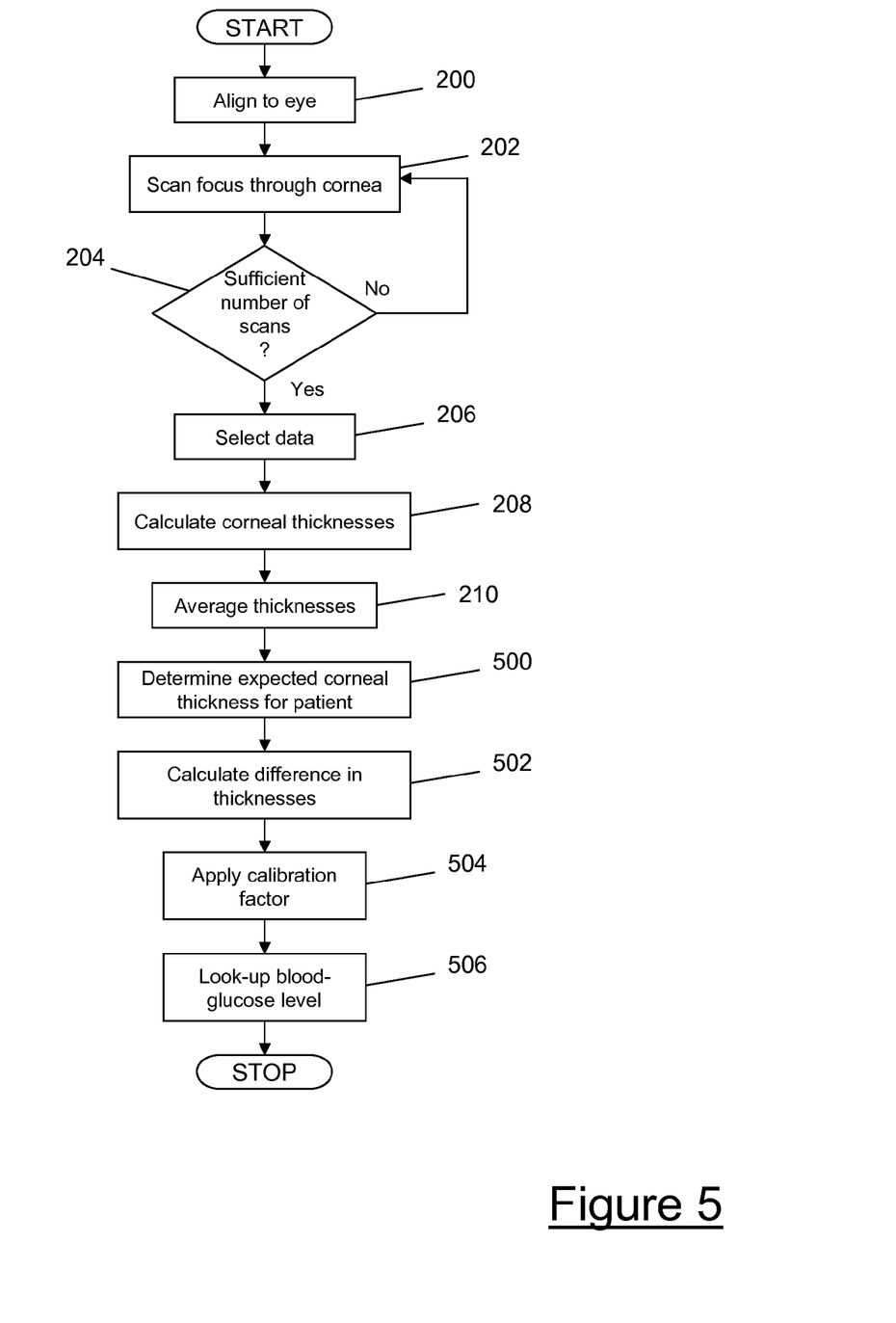
FIG. 5 is a flow diagram of another method of measuring the physiological parameter constituting a second embodiment of the invention.

In another embodiment, the execution of the second alignment and measurement cycle can be avoided by using diurnal data concerning apparent corneal thickness. Turning to FIG. 5, the user holds the measurement apparatus to the eye and starts a measurement procedure by pressing the "measure" button (not shown) on the apparatus as previously described above, which causes the processing resource 134 to initiate an alignment procedure (Step 200) in order to align the optical axis 118 of the optical system 100 to an axis of the eye. As an exemplary alignment technique has already been described above, no further reference will be made in this embodiment to the use of the alignment technique, other than to acknowledge that such a technique can be employed in order to align the optical axis 118 of the optical system 100 to the axis of the eye.

Once aligned, a measurement can be made in respect of the region to be measured 108, now aligned with the optical receiving axis 116 of the optical system 100. In this respect, the techniques set forth in UK patent publication no. GB-B-2 407 378 and/or GB-A-2 409 033 are/is employed to scan (Step 502) a focus of the optical system 100 through the eye 138 to the extent already described above in relation to the previous embodiment. Consequently, in this example, the first collimated probe beam 140 is generated by the first source 102 and folded by the first beamsplitter 104. The folded first beam 140 is thus directed towards the eye 138 along the optical axis 118, propagating through the second beamsplitter 122. Translation of the scanning lens 106 enables the focus of the folded first probe beam 140 to be scanned through the eye 138 in the manner described above.

Referring back to FIG. 3, as the focus of the optical system 100 is scanned through the eye 138, and in particular the region to be measured 108, the first probe beam is reflected, firstly, by the anterior surface 300 of the cornea 302 of the eye 138, and subsequently by the posterior surface 304 of the cornea 302. The time-varying first reflected beam 306 therefore results that passes back through the second beamsplitter 122 and the scanning lens 106. The scanning lens 106 collimates the first reflected beam 306, which passes through the first beamsplitter 104 and is focussed onto the detector 114 via the aperture 112 by the focussing lens 110. The detector 114 translates the first reflected beam 306, constituting an optical signal, from the optical domain into the electrical domain. Consequently, the processor 134 receives an electrical signal in the form of the first time-varying trace 308 comprising localised maxima, for example, peaks created by reflections at the anterior and posterior surfaces 300, 304 of the cornea 302.

The processor 134 then determines (Step 204) whether a sufficient number of scans have been executed for signal processing purposes. In this example, 30 scans are implemented and the resulting first set of traces stored in the storage device 136. However, the skilled person will appreciate that a greater or fewer number of traces can be executed depending upon the signal processing requirements for the use to which the measurement apparatus is to be put.

Once multiple first scans have been executed, the stored first scans are analysed by the processor 134 and first scans that have signal levels within predetermined thresholds are selected (Step 206), the remaining scans being deemed aberrant or inadequate in other ways and rejected. Thereafter, the processor 134 analyses each of the remaining first traces 400 (FIG. 4) and identifies the first localised maximum 402 and the second localised maximum 404 indicative of the reflection of the first probe beam 140 by the anterior surface 300 of the cornea 302 and the posterior surface 304 of the cornea 302, respectively. As part of the analysis, the processor 134 calculates the apparent distance (Step 208) between the first and second localised maxima 402, 404 of each of the remaining first traces 400, the distance corresponding to the apparent thickness of the cornea 302.

Thereafter, the processor 314 averages (Step 210) the distances calculated above to yield an accurate apparent first thickness.

In contrast to the previous embodiment, measurements and calculations in relation to the second averaged apparent thickness of the cornea are not performed in this embodiment. Instead, use is made of diurnal data.

In this respect, it has been observed that the apparent thickness of the cornea of, for example, a human being, varies over the duration of a day due to thinning of the cornea over the course of the day. It is therefore possible to predict the apparent thickness of the cornea of the patient throughout the day. To predict the apparent thickness of the cornea, the processor 134 of the measurement apparatus is coupled to a clock circuit or timer (not shown) in order to provide a time input for use by an expected corneal apparent thickness calculation function (hereinafter referred to as the "expected thickness function"). Additionally, at the beginning of a day, the patient uses the measurement apparatus to measure an initial apparent thickness of the cornea, the measurement apparatus employing the measurement technique already described above to make the initial thickness measurement (Steps 200 to 210). The initial thickness measured in respect of the beginning of the waking day of the patient is also used as an input for the expected thickness function. Consequently, the initial apparent thickness measured is stored in the storage device 136 for use by the expected thickness function. In the event that a patient forgets to make the initial measurement, a measurement can be made subsequent to the time when the initial thickness of the cornea should have been measured and can then be extrapolated using any suitable model in order to calculate the initial thickness of the cornea. During the course of a programme of measurement during a day, the extrapolation process can also or alternatively be used to verify that a current measurement is as expected, a mismatch between a previous measurement and an extrapolated thickness value constituting an unexpected result. The unexpected result can be indicative of a measurement error or a physiological problem being suffered by the patient.

The expected thickness function employs, in this example, an exponential decay algorithm having any decay rate that asymptotically converges upon an expected minimum corneal apparent thickness value. However, a linear model can be employed as an adequate first approximation. The expected minimum corneal thickness is, in this example, obtained by the patient at the end of a day before going to sleep. The expected minimum corneal apparent thickness is also stored by the processor 134 in the storage device 136 and used to calibrate the decay rate used by the expected thickness function. Consequently, the processor 134, using the expected thickness function, is able to calculate (Step 500) the expected corneal apparent thickness at the time the patient is using the measurement apparatus to determine the blood-glucose concentration level. In this respect, when it is time for a subsequent measurement to be made using the measurement apparatus, the expected apparent corneal thickness is also calculated for the time of measurement. The initial corneal thickness and the clock data are used by the expected thickness function to calculate the expected corneal thickness.

After determining the expected corneal thickness, the processor 134 then calculates (Step 502) an apparent thickness difference between the expected corneal thickness calculated for the time at which the measurement is made and the thickness measured using the measurement apparatus. The difference value calculated corresponds to a blood-glucose concentration level of the patient.

Thereafter, the processor 134 then retrieves a calibration factor from the storage device 136 and applies the calibration factor (Step 504) to the difference value calculated to yield a calibrated difference value.

In order to translate the calibrated difference value into a blood glucose concentration value, the processor 134 accesses the storage device 136 and uses, in this example, a look-up table of thickness values and corresponding blood-glucose concentrations, and determines (Step 506) a blood-glucose concentration level corresponding to the calibrated difference value calculated above. Of course, instead of using the look-up table, the blood-glucose concentration value could be obtained by way of a function that calculates the blood-glucose concentration according to a predefined algorithm using the calibrated difference value as an input.

In an alternative embodiment, the fact that the storage device 136 is able to record blood-glucose concentration levels can be used to maintain a record of a patient's blood-glucose concentration level as it varies with time. The data stored can then be downloaded by a physician or other medical profession for subsequent diagnostic purposes. In this respect, a suitable interface can be provided for allowing access to the data. For example, the interface can be wire-line in nature, for example via a Universal Serial Bus (USB) connection, or wireless in nature, for example a Bluetooth™ connection.

Although the above examples have been described in the context of measurement of the thickness of a cornea, the skilled person should appreciate that measurement of the thickness of any suitable volume of a medium is contemplated and/or determination of an apparent changed in thickness thereof. Additionally or alternatively, the skilled person should appreciate that a correlation or regression has been found to exist between the apparent thickness change of the volume of the medium and a blood-glucose concentration, an example of a physiological parameter.

Although the above examples have predominantly been described in the context of the human eye, the skilled person will appreciate that the techniques described herein can be employed, where the context permits, in relation to measurement of any reflecting surface, or surface or region from which a return signal can be obtained, for example from any part of a body, be it human or otherwise. Likewise, measurement of the blood-glucose concentration level for a body is only one example of the physiological parameters that can be measured using the above techniques in relation to the body.

Furthermore, although the above examples have been described in the context of optical measurement, it should be appreciated that alternative systems and techniques for probing the eye in order to determine the thickness of tissue, for example corneal tissue, can be employed, for example through use of different wavelengths of electromagnetic radiation or ultrasound waves. In this respect, it should be appreciated that references herein to "beams" should be interpreted as references to "waves" where the context dictates.

Indeed, it should also be appreciated that references herein to "light", other than where expressly stated otherwise, are intended as references relating to the optical range of the electromagnetic spectrum, for example, between about 350 nm and about 2000 nm, such as between about 550 nm and about 1400 nm or between about 600 nm and about 1000 nm.

It should also be appreciated that the optical system 100 need not be implemented in free space and can be implemented in accordance with a waveguide type design, for example a fibre-optic type design. In this respect, a waveguide arrangement can comprise at least part of the optical system 100.

The optical measurement apparatus can be provided as a portable apparatus for personal or clinical use, for example a hand-held device, or table, desk or bench-top apparatus for a clinical environment where a clinician can be present.

Although reference is made herein to "apparent" thickness and changes in "apparent" thicknesses, the skilled person should understand that it is intended that actual thicknesses and changes in actual thicknesses are intended to be embraced and not only apparent thicknesses and changes thereof due to optical phenomenon, for example changes in refractive index, and/or changes in a visual or other axis, such as optical path change.

Alternative embodiments of the invention can be implemented as a computer program product for use with a computer system, the computer program product being, for example, a series of computer instructions stored on a tangible data recording medium, such as a diskette, CD-ROM, ROM, or fixed disk, or embodied in a computer data signal, the signal being transmitted over a tangible medium or a wireless medium, for example, microwave or infrared. The series of computer instructions can constitute all or part of the functionality described above, and can also be stored in any memory device, volatile or non-volatile, such as semiconductor, magnetic, optical or other memory device.

What is claimed is:

1. A measurement apparatus comprising:
a probe system operably coupled, when in use, to a processing resource;
the probe system and the processing resource are arranged, when in use, to measure an apparent thickness of a volume of corneal tissue referenced at a time, and determine an apparent thickness change thereof in respect of the referenced time;
a storage device arranged to record a correlation or regression between the apparent thickness change of the volume of the corneal tissue and a blood-glucose concentration level;
wherein the processing resource is arranged to access the storage device and to use the measurement of apparent thickness change to determine the blood-glucose concentration level in respect of the referenced time from the correlation or regression accessed;
the probe system comprises a source arranged to emit, when in use, a probe beam and a scanning lens and/or waveguide, wherein the probe system scans the corneal tissue to determine the apparent thickness change thereof.

2. An apparatus as claimed in claim 1, wherein the probe system is an optical system.

3. An apparatus as claimed in claim 1, wherein the apparent thickness change of the volume of the corneal tissue is in respect of a target portion of the corneal tissue.

4. An apparatus as claimed in claim 1, wherein the apparent thickness is between a first surface and a second surface of the corneal tissue.

5. An apparatus as claimed in claim 1, wherein the probe system is arranged to generate a trace in response to electromagnetic radiation received thereby, and the processing resource is arranged to identify a first localised maximum in the trace and a second localised maximum in the trace.

6. An apparatus as claimed in claim 5, wherein the processing resource is arranged to locate the first localised maximum by fitting a first curve thereto and/or the processing resource is arranged to locate the second localised maximum by fitting a second curve thereto.

7. An apparatus as claimed in claim 1, wherein the processing resource is arranged to calculate the apparent thickness change of the volume of the corneal tissue over time.

8. An apparatus as claimed in claim 1, wherein the probe system is arranged to determine a first apparent thickness in respect of the volume of the corneal tissue at a first point in time and a second apparent thickness in respect of the volume of the corneal tissue at a second point in time; and the processing resource is arranged to calculate an integral of the apparent thickness of the volume of the corneal tissue between the first and second points in time.

9. An apparatus as claimed in claim 1, further comprising a data store for recording calibration data, the processing resource being arranged to use the calibration data to compensate for patient-specific corneal thickness when determining the blood-glucose concentration level.

10. An apparatus as claimed in claim 1, wherein the probe system and the processing resource are arranged to use multiple sites on the volume of the corneal tissue to determine the changes in apparent thickness of the volume of the corneal tissue.

11. An apparatus as claimed in claim 10, wherein the probe system is arranged to determine a first apparent thickness in respect of the volume of the corneal tissue at a first point in time and a second apparent thickness in respect of the volume of the corneal tissue at a second point in time; and the multiple sites are employed to generate the first apparent thickness at the first point in time and the same multiple sites are respectively employed to generate the second apparent thickness at the second point in time.

12. An apparatus as claimed in claim 1, wherein the processing resource is arranged to provide an expected apparent thickness of the volume of the corneal tissue at a time of measurement.

13. An apparatus as claimed in claim 12, wherein the processing resource is arranged to employ a function to calculate the change in apparent thickness of the volume of the corneal tissue associated with the blood-glucose concentration level using the expected apparent thickness and a measurement of the apparent thickness of the volume of the corneal tissue.

14. An apparatus as claimed in claim 13, wherein the function is a difference calculation between the expected apparent thickness and the measured apparent thickness.

15. An apparatus as claimed in claim 12, wherein the expected apparent thickness is obtained from a change in apparent thickness of the volume of the corneal tissue over time.

16. An apparatus as claimed in claim 12, wherein the expected apparent thickness is obtained from a data set derived from empirical data of change in apparent thickness of the volume of the corneal tissue over time.

17. An optical measurement apparatus or a glucometer comprising the measurement apparatus as claimed in claim 1.

18. A method of measuring a property of a corneal tissue, comprising;
  probing a volume of the corneal tissue in order to receive a feedback signal;
  measuring an apparent thickness of the volume of the corneal tissue referenced at a time using the feedback signal;
  determining an apparent thickness change of the volume of the corneal tissue in respect of the referenced time;
  accessing a record of a correlation or regression between the apparent thickness change of the volume of the corneal tissue and a blood-glucose concentration level;
  using the measurement of apparent thickness change to determine the blood-glucose concentration level in respect of the referenced time from the correlation or regression accessed and
  wherein the probing comprises scanning the corneal tissue with a probe system comprising a source arranged to emit, when in use, a probe beam and a scanning lens and/or waveguide to determine the apparent thickness change thereof.

* * * * *